(12) United States Patent
Breske et al.

(10) Patent No.: US 12,151,117 B2
(45) Date of Patent: Nov. 26, 2024

(54) WEARABLE CARDIOVERTER DEFIBRILLATOR SYSTEM WITH ELECTRODE MOISTURE SENSING

(71) Applicant: WEST AFFUM HOLDINGS DAC, Dublin (IE)

(72) Inventors: Pamela F. Breske, Newcastle, WA (US); Zoie R. Engman, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 369 days.

(21) Appl. No.: 17/491,322

(22) Filed: Sep. 30, 2021

(65) Prior Publication Data
US 2022/0134120 A1    May 5, 2022

Related U.S. Application Data

(60) Provisional application No. 63/109,772, filed on Nov. 4, 2020.

(51) Int. Cl.
*A61N 1/39* (2006.01)
(52) U.S. Cl.
CPC ......... *A61N 1/3904* (2017.08); *A61N 1/3925* (2013.01)
(58) Field of Classification Search
CPC ............................ A61N 1/3904; A61N 1/3925
See application file for complete search history.

(56) References Cited

U.S. PATENT DOCUMENTS

| 3,724,455 | A | 4/1973 | Unger |
| 4,583,524 | A | 4/1986 | Hutchins |
| 4,619,265 | A | 10/1986 | Morgan et al. |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Bornn et al. |
| 5,353,793 | A | 10/1994 | Bornn |
| RE34,800 | E | 11/1994 | Hutchins |
| 5,394,892 | A | 3/1995 | Kenny |

(Continued)

FOREIGN PATENT DOCUMENTS

| EP | 3380189 B1 | 10/2018 |
| WO | 1998039061 A2 | 9/1998 |
| WO | 2012064604 A1 | 5/2012 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Joseph M Dietrich
(74) *Attorney, Agent, or Firm* — Polsinelli PC

(57) ABSTRACT

Technologies and implementations for a wearable healthcare system, which may detect and determine moisture level at a contact interface between an electrode and a skin of a person. The wearable healthcare system may be a wearable cardioverter defibrillator (WCD) having a moisture sensor at the electrode. The WCD may include moisture providing systems to add moisture material to the contact interface.

14 Claims, 4 Drawing Sheets

(56) References Cited

U.S. PATENT DOCUMENTS

| | | | |
|---|---|---|---|
| 5,405,362 A | 4/1995 | Kramer et al. |
| 5,474,574 A | 12/1995 | Payne et al. |
| 5,618,208 A | 4/1997 | Crouse et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 9,878,171 B2 | 1/2018 | Kaib |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |
| 2019/0192867 A1* | 6/2019 | Savage ............... A61N 1/3925 |
| 2021/0128912 A1* | 5/2021 | Amsler ............... A61N 1/3968 |
| 2022/0054850 A1* | 2/2022 | Umberger ............... G06N 3/02 |

OTHER PUBLICATIONS

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

WEARABLE CARDIOVERTER DEFIBRILLATOR SYSTEM WITH ELECTRODE MOISTURE SENSING

RELATED APPLICATION

This application claims benefit of priority to U.S. Provisional Patent Application Ser. No. 63/109,772, filed on Nov. 4, 2020, titled WEARABLE CARDIOVERTER DEFIBRILLATOR SYSTEM WITH ELECTRODE MOISTURE SENSING, which is incorporated herein by reference in its entirety for all purposes.

INFORMATION

Unless otherwise indicated herein, the approaches described in this section are not prior art to the claims in this application and are not admitted to be prior art by inclusion in this section.

Technology has contributed to improvements in healthcare. Some examples include healthcare related devices that may be mobile and personal. Mobile and personal healthcare devices may include Wearable Medical Devices (WMDs). Some WMDs may include medical devices that facilitate monitoring and treatment of various health related activities of a person. For example, a WMD may include a medical device that may be used to monitor a person's heart activity, including treatment of the heart. The heart activity monitored by the WMD may be in the form of electrical signals (i.e., electrocardiogram or ECG). Treatment of the heart may be in the form of a defibrillating shock, which may be administered responsive to the monitoring detecting a condition to trigger the treatment.

A WMD may be in a mobile form factor such as, but not limited to, a wearable support structure capable of being worn by a person, whose heart activity is to be monitored and/or treated. Having the WMD in a mobile form factor may facilitate continuous monitoring of a person's ECG, which may facilitate detection of heart related issues, including treatment of the heart related issues. Monitoring of the person's ECG may be facilitated by various electrodes on the skin of the person. Contact of the electrodes with the skin may affect the received ECG signal. The contact may be affected by moisture between the electrodes and the skin. Accordingly, the moisture between the electrodes and the skin may affect the monitoring and therapy of the heart related issues.

An example of a WMD in a mobile form factor, which may be used to monitor and facilitate therapy of a person's heart activity, may be a wearable cardioverter defibrillator (WCD). Some examples of WCDs may include various components to facilitate monitoring and treatment of the person's heart such as, but not limited to, electrodes. Some of the electrodes may be configured to monitor the person's heart activity (e.g., electrocardiogram or ECG electrodes) by being placed on the skin of the person. Some of the electrodes may be configured to facilitate providing an electrical shock to the person as treatment (e.g., therapy treatment electrodes). Both the monitoring electrodes and the therapy electrodes may be affected by contact between the electrodes and the skin. An interface property that may affect the contact between the electrodes and the skin may be moisture. For example, little or no moisture between the electrodes and the skin may negatively affect the electrodes from receiving the ECG signal and/or in providing an electric shock.

All subject matter discussed in this section of this document is not necessarily prior art and may not be presumed to be prior art simply because it is presented in this section. Plus, any reference to any prior art in this description is not and should not be taken as an acknowledgement or any form of suggestion that such prior art forms parts of the common general knowledge in any art in any country. Along these lines, any recognition of problems in the prior art are discussed in this section or associated with such subject matter should not be treated as prior art, unless expressly stated to be prior art. Rather, the discussion of any subject matter in this section should be treated as part of the approach taken towards the particular problem by the inventor(s). This approach in and of itself may also be inventive. Accordingly, the foregoing summary is illustrative only and not intended to be in any way limiting. In addition to the illustrative aspects, embodiments, and features described above, further aspects, embodiments, and features will become apparent by reference to the drawings and the following detailed description.

SUMMARY

Described herein are various illustrative Wearable Medical Device (WMD) systems that may include one or more moisture sensors for one or more electrodes in the WMD. The one or more moisture sensors may be configured to trigger the WMD system to dispense moisture material. Example WMD systems may include an indication that may prompt a user to apply moisture material to an area of contact. The electrodes may include electrodes that may be utilized for sensing ECG, providing therapy (e.g., shocks and/or pacing), sensing transthoracic impedance, sensing respiratory rate and/or other physiological activity. The moisture sensors may be incorporated into other types of sensors for which performance can degrade if the skin contacting the sensor gets dry.

The foregoing summary is illustrative only and not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
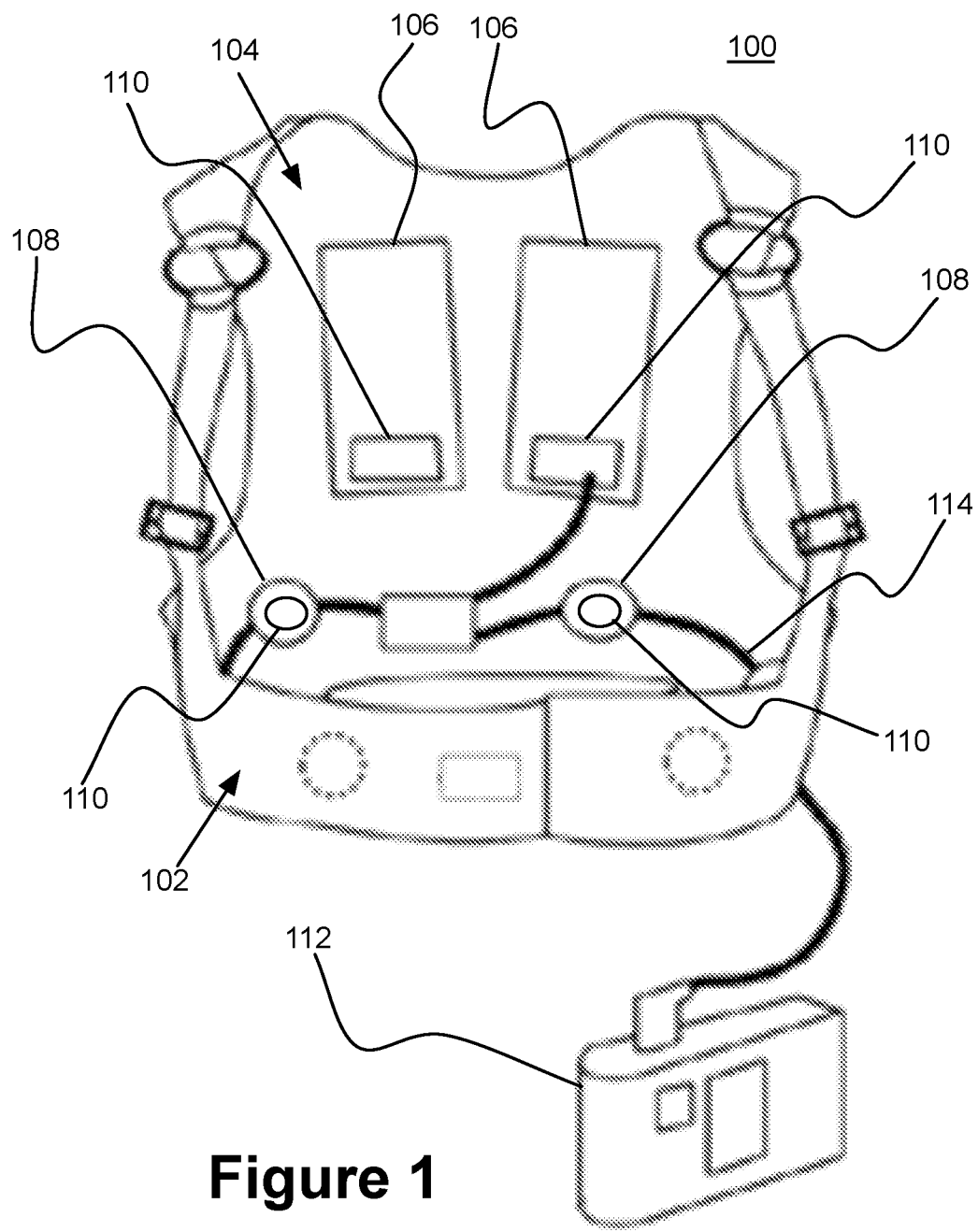
FIG. 1 illustrates a wearable medical device (WMD), in accordance with various embodiments.

The following description sets forth various examples along with specific details to provide a thorough understanding of claimed subject matter. It will be understood by those skilled in the art after review and understanding of the present disclosure, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and systems related to a wearable medical device (WMD) having a moisture sensor for measuring moisture between a person's skin and one or more electrodes. Accordingly, the WMD having a moisture sensor may facilitate improved contact between the person's skin and the one or more electrodes, which in turn may facilitate improved reception of and/or transmission of electrical signals to and from the electrodes.

In the present disclosure, a WMD may include a medical device that may be configured to facilitate monitoring and treatment of potential issues with a person's heart (i.e., the person may have a health condition, where the electrical control system of the heart may malfunction causing the heart to beat irregularly or not at all). Commonly, these types of medical devices may include a defibrillator device (e.g., a wearable cardioverter defibrillator or WCD). In the present disclosure, the WCD may include one or more moisture sensors. Accordingly, the disclosure will be described referencing medical devices having one or more moisture sensors, in accordance with various embodiments.

Before moving on to description utilizing the example of a WCD, it should be appreciated that in some examples, the WMD may be a wide variety of WMDs configured to utilize electrodes for various monitoring activities. Some examples of WMDs may include cardiac event monitors, Holter monitors, mobile cardiac telemetry (MCT) devices, etc. Accordingly, claimed subject matter is not limited in this respect.

Briefly, the above mentioned issue with the rate of the heartbeat may be generally referred to as arrhythmia. Arrhythmia may be caused by many factors, but in general, arrhythmia may be caused by a malfunction in the electrical control system of the heart. Some types of arrhythmias may result in inadequate blood flow resulting in reduction or lack of the amount of blood pumped to the various parts of the body. For example, issues with the sinoatrial (SA) node may lead to arrhythmia of some kind. Some arrhythmias may lead to a condition known as sudden cardiac arrest (SCA). In an SCA condition, the heart may fail to pump blood effectively, and as a result, death may occur.

An example type of arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amounts of blood or may not pump blood at all, which may eventually lead to death. Another type of arrhythmia, which may be associated with SCA, may be a condition known as ventricular tachycardia (VT).

Turning back to the medical device configured to be utilized to help treat VF by defibrillating the heart, the medical device may be capable of monitoring the electrical signals of the person's heart, and if necessary, administer therapy to the heart in the form of an electric shock. The medical device may monitor the electrical signals and provide the electric shock to the heart externally (i.e., through the surface of a body) via components commonly known as electrodes, where some of the electrodes may be monitoring electrodes and some of the electrodes may be therapy electrodes. The medical device may be in the form of a cardioverter defibrillator. The medical device may be included in a support structure configured to be worn by the person. In this example, the medical device may help facilitate monitoring the electrical activities of the person's heart and providing the electric shock to the heart in the VF condition. As a result, the medical device may help prevent Sudden Cardiac Death (SCD).

Since the monitoring of the electrical signals from the person's heart may be received through the surface of the body of the person (i.e., person's skin), the electrodes may be attached to the person's skin. The attachment may be provided by conductive adhesives to facilitate the attachment of the electrodes to the person's skin. In addition to the conductive adhesive, the attachment of the electrodes to the person's skin may be facilitated by the support structure, which may include the electrodes. The electrical signals may be received by the electrodes via a contact interface between the monitoring electrodes and the person's skin. The contact interface may affect the integrity of electrical signals received by the monitoring electrodes. The integrity of electrical signals received by the monitoring electrodes may affect the processing of the electrical signals by the WCD.

Some examples of conductive adhesives may include some form of moisturizer, electrolytic gel, and/or various conductive fluid/moisture material. As will be described in detail, the conductive adhesive may facilitate attachment of the electrodes at the contact interface between the electrodes and the person's skin and maintain and/or promote the integrity of the electrical signals received and/or provided by the electrodes.

Similar to the monitoring electrodes, a contact interface between the therapy electrodes and the person's skin may affect the electrical shock that may be provided to the person's heart. The electrical shock provided to the person's heart may be predetermined to provide enough of an electrical shock to facilitate therapy of the heart. However, if the contact interface is negatively affected, the provided shock may not be the predetermined amount, which may negatively affect the therapy.

Before turning the figures, a non-limiting example scenario may be described. In the non-limiting example scenario, a person may have a heart condition, where the person may utilize a wearable medical device (WMD). The WMD may be configured to facilitate monitoring and treatment of the person's heart condition such as, but not limited to, a wearable cardioverter defibrillator (WCD). The WCD may include a support structure configured to be worn by the person such as, but not limited to, a garment (e.g., a vest). Included in the support structure of the WCD, a WCD monitor may include various components to facilitate the functionality of the WCD. A number of electrodes, monitoring electrodes and therapy electrodes. The electrodes may be communicatively coupled to a WCD monitor, which may include various components to facilitate the functionality of the WCD.

The monitoring electrodes may be disposed on a skin of the person proximate to the person's heart. The monitoring electrodes may be configured to detect and receive electrocardiogram (ECG) signals from the person's heart. Likewise, the therapy electrodes may be disposed on the skin of the person proximate to the person's heart. However, the therapy electrodes may be configured to provide an electrical shock to the person's heart as part of the therapy for a condition of the person's heart. Since the monitoring electrodes and the therapy electrodes may be disposed on the skin to receive and/or deliver electrical signals, a contact interface between the electrodes and the skin may affect the receipt and/or delivery of the electrical signals as described above.

A monitoring electrode may include a sensor that may be disposed at the contact interface. The sensor may be configured to detect the electrical signals of the person's heart (e.g., ECG signals). A therapy electrode may include a shock pad disposed at the contact interface. The shock pad may be configured to deliver an electric shock to the person's heart.

Since the sensor and the shock pad may be reliant upon receipt and/or transmission of electrical signals, the contact interface between the sensor and/or the shock pad may affect the receipt and/or transmission of electrical signals. Some environmental factors may affect the contact interface. For example, the contact interface may be affected by moisture. If the contact interface has less moisture, the contact interface between the sensor and/or the shock pad and the skin may be negatively affected (i.e., integrity of the ECG signal may be negatively affected and/or the delivery of the electrical shock therapy may be negatively affected).

Continuing with the non-limiting scenario, in one example, the WCD may include a moisture sensor. The moisture sensor may be included with the electrodes (e.g., included with the monitoring electrode and/or the therapy electrode). The moisture sensor may be configured to sense the moisture of the skin at the contact interface between the electrode and the skin. In one example, the moisture sensor may be simple as to detect the presence of moisture (e.g., when moisture is present, the sensor may change color). In another example, the moisture sensor may be configured to determine a level of moisture at the contact interface (e.g., an electronic device, which may be configured to utilize impedance measurements). In the non-limiting scenario, the moisture sensor may be an electronic device configured to determine the presence of and/or the level of moisture at the interface of the electrode and the skin.

Continuing with the non-limiting scenario, an electrode (i.e., either or both the monitoring electrode and the therapy electrode) may include the moisture sensor configured to determine the presence of and/or the level of moisture at the contact interface of the electrode and the skin. For this example, the moisture sensor may be configured to determine the level of moisture at the contact interface of the electrode and the person's skin.

As the person wears the WCD as prescribed, the contact interface of the electrode and the person's skin may begin to dry out (i.e., reduction of moisture). In one example, a predetermined level may be set by the WCD manufacturer for optimum electrical contact. If the moisture level falls to the predetermined level, the moisture sensor may provide a communicative signal to the WCD monitor. Responsive to the received communicative signal from the moisture sensor, the WCD monitor may be configured to provide an indication. The indication may be a variety of indications such as, but not limited to, a visual indication (e.g., a light), an audio indication (e.g., a sound), a visual display indication (e.g., information on a display, which may or may not be a user interface type display).

In one example, the WCD may include a light emitting diode (LED), which may be utilized to provide an indication of the moisture level being at the predetermined level (e.g., low moisture). In another example, the WCD may include a speaker, which may be utilized to provide an indication of the moisture level being at the predetermined level. In yet another example, the WCD may include a display, which may be utilized to provide a graphical indication of the moisture level. The graphical indication may be displayed on a user interface, which may provide a graphical representation of the moisture level being at various levels. The indication of the low moisture level may facilitate addressing the low moisture level (e.g., adding moisture to the contact interface of the electrode), which may help to maintain good electrical contact between the skin and the electrode.

Adding/applying the moisture to the contact interface between the electrode and the skin may be achieved utilizing several methodologies. In some examples, a moisture material such as but not limited to electrolyte gel, moisturizer, skin lotion, water, etc. may be added/applied to the contact interface manually (i.e., by a person, the person wearing the WCD, assistance personnel, medical personnel, etc.). In some other examples, the moisture may be added/applied to the contact area utilizing an apparatus that may be configured to facilitate addition/application of moisture (i.e., moisture material). Adding/applying the moisture may address the indication of the low moisture level (e.g., turn off the visual and/or audio indications and/or graphically indicate a moisture level, which may be acceptable).

As will be described in detail, the example of an apparatus, that may be utilized to add/apply moisture material to the contact interface, may include a fluid reservoir configured to be disposed on the electrode. The fluid reservoir may have the moisture material. In this example, the electrode may include features (e.g., fluid channels/ports) to facilitate flow of the moisture material from the fluid reservoir to the contact interface. Additionally, the apparatus may include a fluid housing to provide moisture material to the fluid reservoir. The fluid housing may facilitate replenishment of the fluid reservoir by providing moisture material via a fluid tube coupled between the fluid housing and the fluid reservoir.

In one example, the flow of the moisture material from the fluid reservoir to the contact interface may be facilitated by opening and closing of the fluid channels/ports, where the opening and closing may be facilitated by electrically controlling the fluid channel/ports (e.g., microvalves). In another example, the flow of moisture material from the fluid reservoir to the contact interface may be facilitated by pressure of the moisture material included in the fluid reservoir (e.g., pressure that may facilitate the flow of moisture material into the channel/ports). The pressure may be provided by the fluid housing pushing moisture material to the fluid reservoir.

Continuing with the non-limiting example scenario, the person may be wearing the WCD, and the moisture sensor may detect that the moisture level at one or more electrodes has fallen below the predetermined level. Responsive to the detected moisture level, the WCD may provide an audio sound (e.g., beeping sound). The person may see the moisture level on a display included with the WCD monitor. In one example, the person may activate an interface (e.g., physical button and/or touch screen) to activate flow of moisture material to the contact interface at the electrode, where the flow of moisture may be facilitated as described above. In another example, the WCD may automatically address the low moisture level (i.e., electrically open the fluid channels/ports at the fluid reservoir and/or electrically push moisture material from the fluid housing to the fluid reservoir). Automated addressing of the low moisture level may be facilitated by the WCD monitor.

As a result, the moisture level at the contact interface at the electrode and the person's skin may be maintained to help facilitate prevention of negative effects on the electrical contact between the electrode and the skin (i.e., not negatively affect the electrical signals such as ECG or electrical shock).

Turning now to FIG. 1, FIG. 1 illustrates a wearable medical device (WMD), in accordance with various embodiments. In FIG. 1, a WMD may be configured to facilitate monitoring and treatment of a person's heart such as, but not limited to, a wearable cardioverter defibrillator (WCD) 100. The WCD may be in the form of a clothing configured to be worn by a user such as, but not limited to, a vest type. Accordingly, the WCD 100 may have a front side 102 and a back side 104 forming the vest type WCD 100 as shown. Additionally, the WCD 100 may include one or more electrodes configured to defibrillate the person's heart, defibrillator electrodes (therapy electrodes 106) and one or more electrodes configured to detect and measure the person's electrocardiogram (ECG), monitor electrodes 108. In FIG. 1, the therapy electrodes 106 and the monitor electrodes 108 may each include a moisture sensor 110.

It should be appreciated after review of this disclosure that the locations of the therapy electrodes 106 may be shown in various configurations such as, but not limited to, one front and one back, across a chest, across a back, etc. to facilitate defibrillation, and accordingly, the locations of the therapy electrodes 106 and/or the monitor electrodes 108 in FIG. 1 may be for illustrative purposes to show that there may be some electrodes to facilitate operation of the WCD 100. Additionally, for the purposes of the detailed description, references may be made to "an electrode", which may be any one of electrodes (therapy electrodes 106 and/or monitor electrodes 108) to provide the functionality of the WCD 100.

Continuing to refer FIG. 1, the WCD 100 may include a WCD monitor 112. In the example shown in FIG. 1, the WCD monitor 112 may be communicatively coupled to the therapy electrodes 106 and/or monitor electrodes 108 via one or more wires 114. However, in some other examples, the WCD monitor 112 may be integrated with the WCD such as, but not limited to, the back side 104. The WCD monitor 112 may include various components to facilitate the functionality of the WCD 100 (i.e., monitor and defibrillate the person's heart) such as, but not limited to, a processor, memory, power supply (e.g., battery), a display, etc. Some of these components may be described in further detail later in the disclosure.

In FIG. 1, the WCD 100 may the moisture sensor 110 may detect that the moisture level at one or more electrodes (e.g., the therapy electrodes 106 and/or monitor electrodes 108) has fallen below a predetermined level. The WCD monitor 112 may receive the detected signal from the moisture sensor 110. The WCD monitor 112 may process the received signal, and responsive to the processed signal from the moisture sensor 110, the WCD monitor may provide an indication (e.g., audio, visual, display, etc.) as previously described.

It should be appreciated that the example WCD 100 shown in FIG. 1 may be in the form of a vest. However, the WCD 100 may be in the form of a wide variety of clothing such as, but not limited to, a jacket, a t-shirt, a dress shirt, a belt, a blouse, a coat, and any combination thereof. Accordingly, the components of the WCD 100 may be integrated with a wide variety of wearable clothing.

The moisture sensor 110 may be a variety of moisture sensors such as, but not limited to, flexible sensors. Some examples of flexible sensors may be of the kind available from Axzon Corporation of Austin, Texas. In some examples, the moisture sensor 110 may be impedance based type sensor (i.e., dry skin may cause a higher impedance, which may be measured and processed into a moisture level by the WCD monitor 112). Accordingly, the claimed subject matter is not limited in this respect.

Figures 2A, 2B:
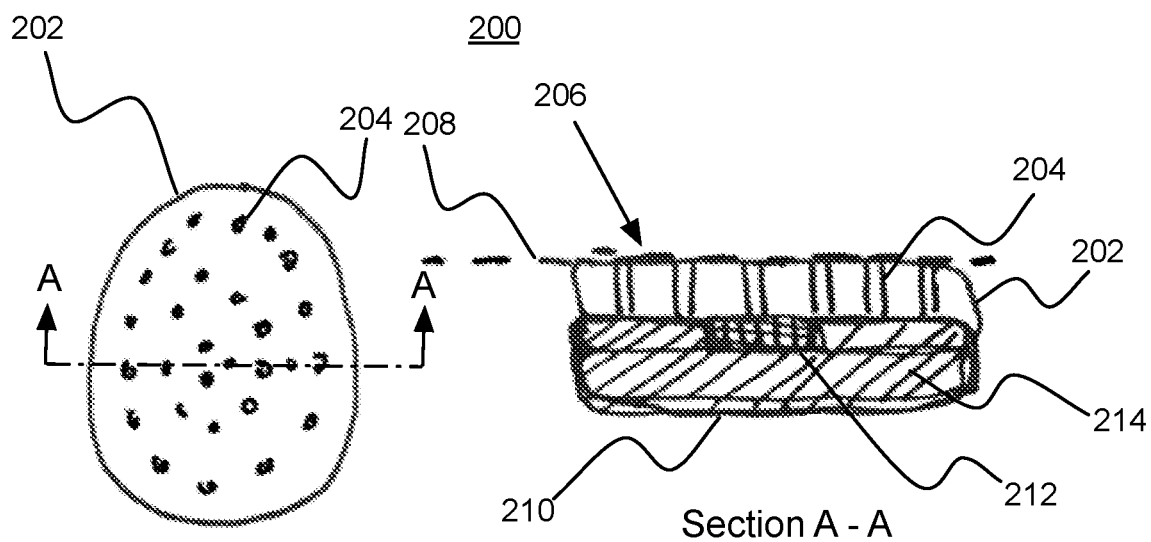
FIGS. 2A and 2B illustrate an apparatus for maintaining moisture at a contact interface between an electrode and a person's skin, in accordance with various embodiments.

FIGS. 2A and 2B illustrate an apparatus for maintaining moisture at a contact interface between an electrode and a person's skin, in accordance with various embodiments. In FIG. 2A, illustrates a top view of an electrode moisture apparatus 200, and FIG. 2B illustrate a cross-section A-A of the electrode moisture apparatus 200. In FIGS. 2A and 2B, an electrode 202 may include a number of fluid channels/ports 204. The fluid channels/ports 204 may facilitate providing moisture material to a contact interface 206 between a skin 208 and the electrode 202. Additionally, the electrode 202 may include a fluid reservoir 210. In the example shown in FIGS. 2A and 2B, the fluid reservoir 210 may be configured to snap on the electrode 202. This snap on configuration may be facilitated by a connector 212. Additionally, the connector 212 may be configured to facilitate the flow of a moisture material 214 from the fluid reservoir 210 to the fluid channels/ports 204.

As shown in FIGS. 2A and 2B, as previously described in the above non-limiting scenario, the electrode moisture apparatus 200 may facilitate maintaining a moisture level at the contact interface 206 to help facilitate prevention of negative effects on the electrical contact between the electrode 202 and the skin 208 (i.e., not negatively affect the electrical signals such as ECG or electrical shock).

The to the fluid channels/ports 204 may be a wide variety of fluid channels/ports such as active (i.e., can open and close) and/or passive (i.e., open holes). Some examples of active channels/ports may include, but not limited to, piezoelectric type micro valves such as those that may be available from CTS Corporation of Albuquerque, New Mexico. Accordingly, the claimed subject matter is not limited in this respect.

Figure 3:
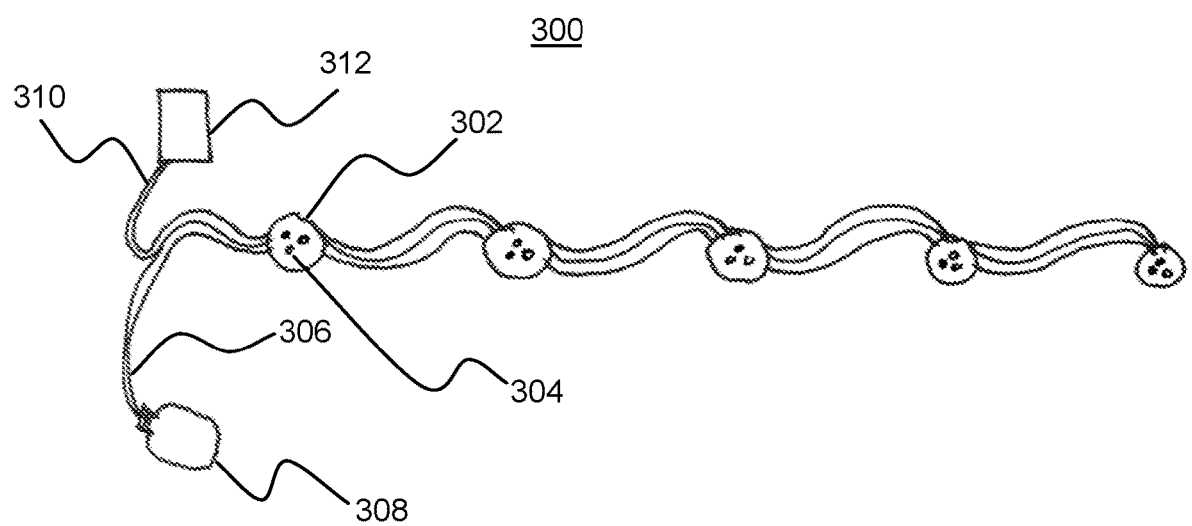
FIG. 3 illustrates an example moisture apparatus to facilitate operation of an electrode moisture apparatus, in accordance with various embodiments.

FIG. 3 illustrates an example moisture apparatus to facilitate operation of an electrode moisture apparatus, in accordance with various embodiments. In FIG. 3, a moisture apparatus 300 may include one or more electrode moisture apparatus 302 such as those shown in FIGS. 2A and 2B. The one or more electrode moisture apparatus 302 may include fluid channels/ports 304. As shown, the one or more electrode moisture apparatus 302 may be coupled to each other by a fluid tube 306. The fluid tube 306 may have coupled to it, a fluid housing 308. The fluid housing 308 may hold the moisture material such as the moisture material 214 shown in FIG. 2B. Additionally, the moisture apparatus 300 may include an electrical wire 310 communicatively coupling the one or more electrode moisture apparatus 302. The electrical wire 310 may be communicatively to an electrical housing 312, which may be included or communicatively coupled to a WCD monitor such as the WCD monitor 112 shown in FIG. 1.

In FIG. 3, the moisture apparatus 300 may provide the moisture material to the one or more electrode moisture apparatus 302 via the fluid tube 306. As described in the above non-limiting example scenario, in some examples, the moisture material may be provided manually by application of pressure on the fluid housing 308. In some other examples, the moisture material may be provided automatically under the control of the electrical housing 312 (i.e., the fluid housing 308 and/or the one or more electrode moisture apparatus 302 may be electrically controlled including the fluid channels/ports 304). In yet some other examples, the fluid tube 306 may be configured to provide moisture material directly to the contact interface (i.e., the one or more electrode apparatus may not include a fluid reservoir). In some examples, fluid tube 306 may be configured to provide moisture material to the fluid reservoir to facilitate replenishing the fluid reservoir. Accordingly, the claimed subject matter is not limited in these respects.

As a result, a moisture level at the contact interface at an electrode and the person's skin may be maintained to help facilitate prevention of negative effects on an electrical contact between the electrode and the skin (i.e., not negatively affect the electrical signals such as ECG or electrical shock), in accordance with various embodiments.

Figure 4:
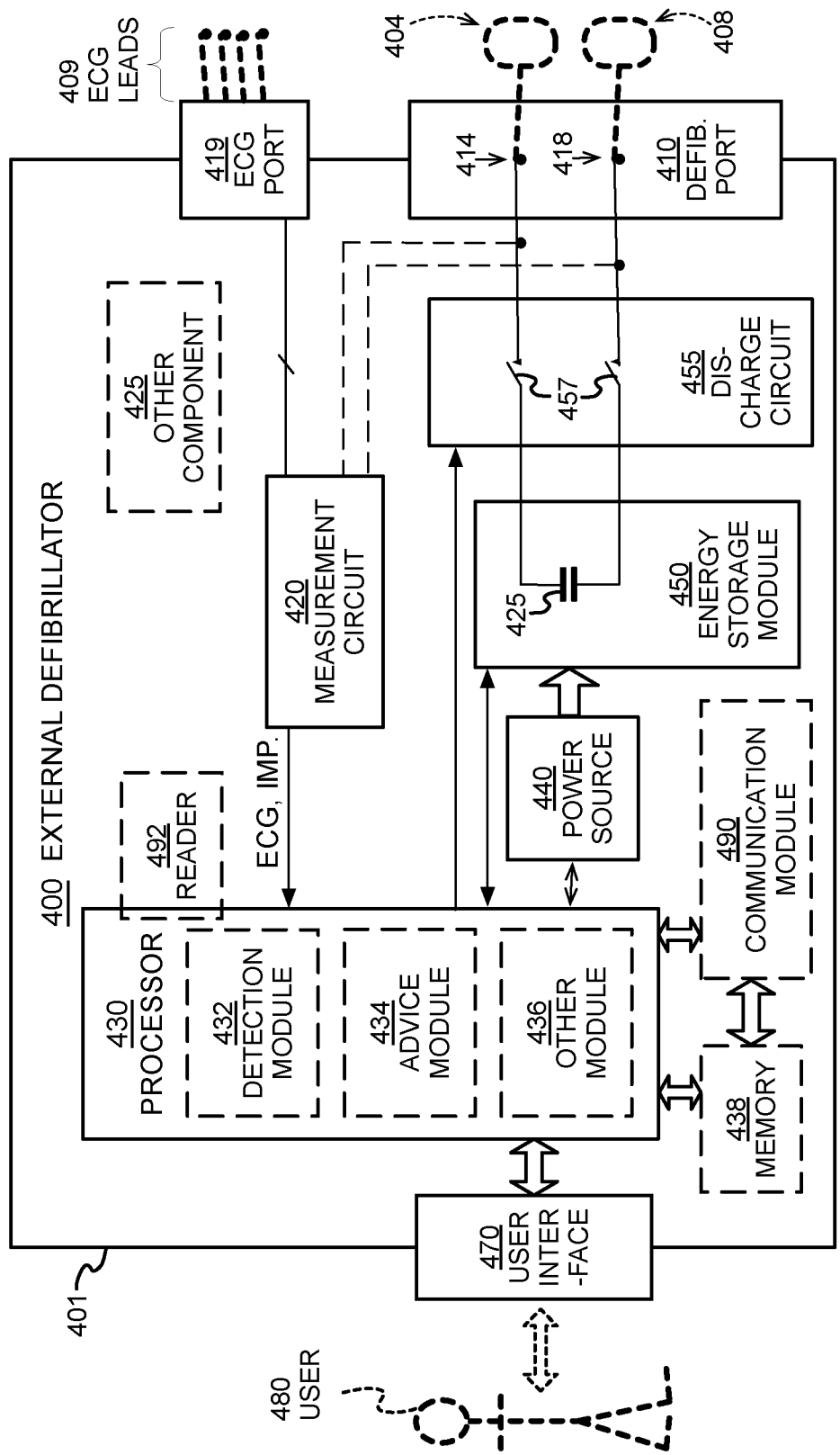
FIG. 4 is a block diagram illustrating components of WCD having moisture sensing and compensating systems, in accordance with various embodiments.

FIG. 4 is a block diagram illustrating components of WCD having moisture sensing and compensating systems, in accordance with various embodiments. These components may be, for example, components of medical device such as, but not limited to, a WCD 100.

The defibrillator device 400 may be some of the above examples of a one or more modules for the medical device intended for use by a user 480 (e.g., a wearer, a person, a patient, etc.). The defibrillator device 400 may typically include a defibrillation port 410, such as a socket in housing 401. The defibrillation port 410 may include nodes 414 and 418. One or more electrodes 404 and 408, which may be removably plugged into the defibrillation port 410, so as to make electrical contact with nodes 414 and 418, respectively. It may also be possible that the electrodes 404 and 408 may be connected continuously to the defibrillation port 410, etc. Either way, the defibrillation port 410 may be used for guiding via the electrodes 404 and 408 to a person 404 an electrical charge that may have been stored in the defibrillator device 700, as described herein.

The defibrillator device 400 may also have an ECG port 419 in the housing 401, for receiving ECG cables 409. The ECG cables 409 may facilitate sensing of an ECG signal (e.g., a 12-lead signal or from a different number of lead signals). Moreover, a defibrillator-monitor could have additional ports (not shown) making the defibrillator device 400 more reconfigurable, and a moisture sensing component 425 may be configured to determine a moisture level at a contact interface between an electrode and a skin. In some examples, there may be additional components configured to filter the ECG signal (e.g., application of at least one filter to the signal to help facilitate removal of artifacts such as, but not limited to, chest compression due to chest compressions being delivered to the person).

The defibrillator 400 also may include a measurement circuit 420. The measurement circuit 420 may receive physiological signals from the ECG port 419, and also from other ports, if provided. The circuit 420 may render detected physiological signals and their corresponding information. The information may be in the form of data, or other signals, etc.

The measurement circuit 420 may obtain physiological signals through the nodes 414 and 418, when the electrodes 404 and 408 are attached to the person. In these cases, a person's ECG signal may be detected as a voltage difference between the electrodes 404 and 408. Additionally, the impedance between the electrodes 404 and 408 may be detected, among other things, whether the electrodes 404 and 408 have been inadvertently disconnected from the person.

The defibrillator 400 may also include a processor 430. The processor 430 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 430 may include a number of modules. One example module may be a detection module 432, which may detect outputs from the measurement circuit 420. The detection module 432 may include a VF detector. Accordingly, the person's detected ECG may be utilized to help determine whether the person is experiencing ventricular fibrillation (VF).

In another example module may be an advice module 434, which may provide advice based, at least in part, on outputs of detection module 432. The advice module 434 may include an algorithm such as, but not limited to, Shock Advisory Algorithm, implement decision rules, and so on. For example, the advice may be to shock, to not shock, to administer other forms of therapy, and so on. If the advice is to shock, some defibrillator examples may report the advice to the user, and prompt them to do it. In other examples, the defibrillator device may execute the advice by administering the shock. If the advice is to administer CPR, the defibrillator 400 may further issue prompts for administrating CPR, and so forth.

The processor 430 may include additional modules, such as motion analysis module 436 for various motion related functions described herein. Additionally, if other motion sensing component 425 is provided, it may be operated in part by processor 430, etc.

In an example, the defibrillator device 400 may include a memory 438, which may work together with the processor 430. The memory 438 may be implemented in a wide variety of manners. For example, the memory 438 may be implemented such as, but not limited to, nonvolatile memories (NVM), read-only memories (ROM), random access memories (RAM), and so forth or any combination thereof. The memory 438 may can include programs for the processor 430, and so on. The programs may include operational programs execution by the processor 430 and may also include protocols and methodologies that decisions may be made by advice module 434. Additionally, the memory 438 may store various prompts for the user 480, etc. Moreover, the memory 438 may store a wide variety of information (i.e., data) such as, but not limited to information regarding the person.

The defibrillator 400 may also include a power source 440. In order to facilitate portability of defibrillator device 400, the power source 440 may include a battery type device. A battery type device may be implemented as a battery pack, which may be rechargeable or not be rechargeable. At times, a combination of rechargeable and non-rechargeable battery packs may be utilized. Additionally, the power source may be configured to be modified to accommodate the power level demands (e.g., monitoring mode without therapy or vice versa). Examples of power source 440 may include AC power override, where AC power may be available, and so on. In some examples, the processor 430 may control the power source 440.

Additionally, the defibrillator device 400 may include a configurable energy storage module 450. The configurable energy storage module 450 may be configured to store some electrical energy (e.g., when preparing for sudden discharge to administer a shock). The configurable energy storage module 450 may be charged from the power source 740 to an appropriate level of energy, as may be controlled by the processor 430. In some implementations, the configurable energy storage module 450 may include one or more capacitors 452, and the like.

The defibrillator 400 may include a discharge circuit 455. The discharge circuit 455 may be controlled to facilitate discharging of the energy stored in energy storage module 450 to the nodes 414 and 418, and also to electrodes 404 and 408. The discharge circuit 455 may include one or more switches 457. The one or more switches 457 may be configured in a number of manners such as, but not limited to, an H-bridge, and so forth.

The defibrillator device 400 may further include a user interface 470 for the user 480. The user interface 470 may be implemented in a variety of manners. For example, the user interface 470 may include a display screen capable of displaying what is detected and measured, provide visual feedback to the user 480 for their resuscitation attempts, and so forth. The user interface 470 may also include an audio output such as, but not limited to, a speaker to issue audio prompts, etc. The user interface 470 may additionally include various control devices such as, but not limited to, pushbuttons, touch display, and so forth. Additionally, the discharge circuit 455 may be controlled by the processor 430 or directly by the user 480 via the user interface 470, and so forth.

Additionally, the defibrillator device 400 may include other components. For example, a communication module 490 may be provided for communicating with other machines and/or the electrodes. Such communication may be performed wirelessly, or via wire, or by infrared communication, and so forth. Accordingly, information may be communicated, such as person data, incident information, therapy attempted, CPR performance, ECG information, and so forth.

The above described components may be configured and reconfigured, in accordance with various embodiments. For example, monitoring mode or monitoring and therapy mode.

It should be appreciated after review of this disclosure that it is contemplated within the scope and spirit of the present disclosure that the claimed subject matter may include a wide variety of healthcare devices. Accordingly, the claimed subject matter is not limited in these respects.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter is not limited to the particular examples disclosed, but that such claimed subject matter also may include all implementations falling within the scope of the appended claims, and equivalents thereof.

What is claimed:

1. A wearable cardioverter defibrillator (WCD) system for use by a person, the WCD system comprising:
   a WCD monitor;
   an electrode communicatively coupled to the WCD monitor, the electrode configured to contact a skin of the person when wearing the WCD;
   a moisture sensor included in the electrode, the moisture sensor configured to detect a moisture level at an interface between the electrode and the skin;
   a moisture reservoir coupled to the electrode, the moisture reservoir configured to store moisturizing material; and
   a moisture management module configured to automatically control the moisture reservoir to transport the moisturizing material from the moisture reservoir to the interface between the electrode and the skin, in response to the moisture sensor detecting the moisture level below a threshold level.

2. The WCD system of claim 1, further comprising a support structure adapted to position the electrode on the skin when worn by the person.

3. The WCD system of claim 1, wherein the electrode comprises a monitor electrode configured to receive electrocardiogram (ECG) signals.

4. The WCD system of claim 1, wherein the electrode is used in providing an electric shock from the WCD monitor to the person.

5. The WCD system of claim 1, wherein the moisture sensor comprises a device configured to detect the presence or absence of moisture.

6. The WCD system of claim 1, wherein the moisture sensor comprises an impedance device.

7. The WCD system of claim 1, wherein the moisture sensor comprises a wireless moisture sensor.

8. The WCD system of claim 7, wherein the wireless moisture sensor comprises a radio frequency identification (RFID) moisture sensor.

9. The WCD system of claim 1, wherein the moisture reservoir is coupled to the electrode via a tube that is configured to transport the moisturizing material from the moisture reservoir to the electrode.

10. The WCD system of claim 9, further comprising a moisture port coupled with the electrode, the moisture port configured to provide the moisturizing material from the moisture reservoir to the interface between the electrode and the skin.

11. A wearable medical device (WMD) system for use by a person, the WMD system comprising:
    a WMD monitor;
    an electrode communicatively coupled to the WMD monitor, the electrode configured to contact a skin of the person when wearing the WMD;
    a moisture sensor included in the electrode, the moisture sensor configured to detect a moisture level at an interface between the electrode and the skin;
    a moisture reservoir coupled to the electrode, the moisture reservoir configured to store moisturizing material; and
    a moisture management module configured to automatically control the moisture reservoir to transport the moisturizing material from the moisture reservoir to the interface between the electrode and the skin, in response to the moisture sensor detecting the moisture level below a threshold level.

12. The WMD system of claim 11, wherein the WMD comprises a mobile cardiac telemetry (MCT) device.

13. The WMD system of claim 11, wherein the WMD comprises a Holter monitor device.

14. The WMD system of claim 11, wherein the WMD monitor is configured to provide an indication, in response to the moisture sensor detecting the moisture level below the threshold level.

* * * * *